United States Patent
Pfrang

(10) Patent No.: US 10,314,975 B2
(45) Date of Patent: Jun. 11, 2019

(54) DEVICE FOR ADMINISTRATION OF A PHARMACEUTICAL

(71) Applicant: Gerresheimer Regensburg GmbH, Regensburg (DE)

(72) Inventor: Juergen Pfrang, Kallmuenz (DE)

(73) Assignee: Gerresheimer Regensburg GMBH, Regensburg (DE)

( * ) Notice: Subject to any disclaimer, the term of this patent is extended or adjusted under 35 U.S.C. 154(b) by 436 days.

(21) Appl. No.: 14/730,064

(22) Filed: Jun. 3, 2015

(65) Prior Publication Data
US 2015/0352281 A1    Dec. 10, 2015

(30) Foreign Application Priority Data

Jun. 4, 2014   (DE) .................. 10 2014 107 859

(51) Int. Cl.
*A61M 15/00*      (2006.01)
*A61M 5/178*      (2006.01)
(Continued)

(52) U.S. Cl.
CPC ............. *A61M 5/178* (2013.01); *A61M 5/20* (2013.01); *A61M 5/3135* (2013.01);
(Continued)

(58) Field of Classification Search
CPC .. A61M 2205/8243; A61M 2205/8237; A61M 2205/825; A61M 15/00;
(Continued)

(56) References Cited

U.S. PATENT DOCUMENTS 5,809,997 A * 9/1998 Wolf .................. A61M 15/009
                                                   128/200.23
6,202,642 B1 * 3/2001 McKinnon .......... A61M 15/009
                                                   128/200.14
(Continued)

FOREIGN PATENT DOCUMENTS

EP         2 662 008 A2    11/2013
WO      2007/137991        12/2007
(Continued)

OTHER PUBLICATIONS

Energy Harvesting, from Wikipedia, Oct. 28, 2014, 13 pages.
(Continued)

*Primary Examiner* — Colin W Stuart
*Assistant Examiner* — Douglas Y Sul
(74) *Attorney, Agent, or Firm* — Leydig, Voit & Mayer, Ltd.

(57) ABSTRACT

The invention relates to a device for administration of a pharmaceutical with
   a) a reservoir (1) for storage of the pharmaceutical, wherein the reservoir (1) has a dispensing opening (2),
   b) a trigger means (3) for triggering an administration of a pharmaceutical, in which the pharmaceutical is dispensed through the dispensing opening (2),
   c) an information storage medium (4) for storage of administration data,
wherein
   d) a converter means (5) for converting analog administration data into digital administration data,
   e) a wireless information transmitter means (6) for transmitting the administration data to an external display and/or storage medium, and
(Continued)

e) a power generator means (7) for providing electrical power for the converter means (5), information storage medium (4) and/or the information transmitter means, are provided.

12 Claims, 5 Drawing Sheets

(51) Int. Cl.
*A61M 5/20* (2006.01)
*A61M 5/31* (2006.01)
*A61M 5/315* (2006.01)

(52) U.S. Cl.
CPC ...... *A61M 5/31511* (2013.01); *A61M 15/008* (2014.02); *A61M 15/009* (2013.01); *A61M 2005/3126* (2013.01); *A61M 2205/3561* (2013.01); *A61M 2205/3576* (2013.01); *A61M 2205/3592* (2013.01); *A61M 2205/50* (2013.01); *A61M 2205/52* (2013.01); *A61M 2205/60* (2013.01); *A61M 2205/82* (2013.01); *A61M 2205/825* (2013.01); *A61M 2205/8206* (2013.01); *A61M 2205/8237* (2013.01); *A61M 2205/8243* (2013.01)

(58) Field of Classification Search
CPC ............ A61M 15/008; A61M 15/0005; A61M 2205/3592; A61M 2005/3126
See application file for complete search history.

(56) References Cited

U.S. PATENT DOCUMENTS

| | | | |
|---|---|---|---|
| 6,958,691 B1* | 10/2005 | Anderson | A61B 5/0002 128/200.14 |
| 8,975,764 B1* | 3/2015 | Abehasera | F03G 7/08 128/202.21 |
| 2005/0028815 A1* | 2/2005 | Deaton | A61M 15/0065 128/200.23 |
| 2008/0132881 A1 | 6/2008 | Wood et al. | |
| 2009/0194104 A1* | 8/2009 | Van Sickle | A61M 15/00 128/203.12 |
| 2010/0252036 A1* | 10/2010 | Sutherland | A61M 15/00 128/203.12 |
| 2013/0053719 A1* | 2/2013 | Wekell | A61B 5/09 600/539 |
| 2013/0300350 A1* | 11/2013 | Xiang | A24F 47/00 320/108 |
| 2014/0144946 A1 | 5/2014 | Kohnle et al. | |

FOREIGN PATENT DOCUMENTS

| | | |
|---|---|---|
| WO | 2012/100431 | 8/2012 |
| WO | 2014/006413 | 1/2014 |
| WO | 2014/068504 | 5/2014 |

OTHER PUBLICATIONS

German Office Action, dated Oct. 29, 2014, in German Patent Application No. 10 2014 107859.4, a related application, 6 pp.
First Chinese Office Action, dated Dec. 25, 2017, in Chinese Patent Application No. 2015102988551, a related application, 28 pp.

* cited by examiner

DEVICE FOR ADMINISTRATION OF A PHARMACEUTICAL

CROSS-REFERENCE TO RELATED APPLICATIONS

This application is a U.S. Nonprovisional Application filed under 35 U.S.C. § 111(a) which claims the benefit of German Application No. 10 2014 107 859.4, filed Jun. 4, 2014, which is hereby incorporated by reference in its entirety.

BACKGROUND

The invention relates to a device for administration of a pharmaceutical according to the preamble of claim 1.

A device of this type for administration of a pharmaceutical is known for example from US 2006/0011651 A1. The device disclosed there for administration of a pharmaceutical is an inhaler with a reservoir for storage of the pharmaceutical, the reservoir having a dispensing opening. Furthermore, this device has a trigger means for triggering an administration of a pharmaceutical, the pharmaceutical being dispensed through the dispensing opening. Furthermore, this device has an information storage medium for storage of administration data, the device being provided in this case with an electronic display. In this respect, this display is of a permanent type, so that no current is required in order to keep the display unchanged. Furthermore, only a very low current is necessary in order to modify the display. In this case, the display may be a liquid crystal display or may comprise bistable nematic crystals.

Although devices of this type already operate in a very energy-efficient manner, they have to be operated with a power storage unit. Such power storage units do operate independently of an external power supply, but are primarily designed as batteries. Because of self-discharge these batteries can make replacement necessary over the possibly very long life-cycle of the device. The possibility also exists that batteries of this type can be designed to be considerably larger, but this leads to a greater weight and a greater volume of the device. Furthermore, due to the use of batteries a disposal process is also required which is not always insignificant.

It is also possible to use rechargeable accumulators. However, this is not generally accepted by users, since it involves additional actions by the user due to the charging of the accumulators and the activities associated therewith. In addition, the use of accumulators can also lead to safety-related problems, since for example because of discharging of the accumulators an electronic dosing meter no longer functions correctly and an excessively large residual amount of pharmaceutical in the reservoir is possibly displayed to the user. In this respect, the user may not be prepared to have an additional reservoir with a pharmaceutical ready if the reservoir contained in the device is already empty.

SUMMARY

Furthermore, the administration data relating to the administrations which have been carried out are only contained in the device, so that these data may be lost if the power supply fails.

Therefore the object of the invention is to further develop a device for administering a pharmaceutical according to the preamble of claim 1 in such a way that operation of the device is maintained independently of a replaceable battery or replaceable accumulator respectively and the administration data can be stored securely with regard to administrations which have already been carried out with the device.

This object is achieved by a device for administration of a pharmaceutical having all the features of claim 1. Advantageous embodiments of the invention are set out in the subordinate claims.

The device according to the invention for administration of a pharmaceutical is provided in this respect with a reservoir for storage of the pharmaceutical, the reservoir having a dispensing opening. Furthermore, the device has a trigger means for triggering an administration of a pharmaceutical, in which the pharmaceutical is dispensed through the dispensing opening. Furthermore, an information storage medium which serves for storage of administration data is integrated in the device. The device according to the invention is now characterised in that firstly a converter means for converting analogue administration data into digital administration data, a wireless information transmitter means for transmitting the administration data to an external display and/or storage medium and a power generator means for providing electrical power for the converter means and the information transmitter means are provided.

In this respect, instead of a long-term power storage unit in the form of a battery or an accumulator, with the aid of the power generator it is possible just before or during administration of the pharmaceutical respectively to obtain the required power and to make the converter means and the wireless information transmitter means available. In this respect, the converter means converts analogue administration data, for example in the form of administration doses and times, into digital administration data which are then relayed by means of the wireless information transmitter means to an external display and/or storage medium.

Due to the invention, a device of this type becomes independent of a power supply or is self-sufficient in power, since during operation the device itself can generate or provide the power necessary for operation. Furthermore, due to the invention it also does not have to be ensured that the administration data are permanently stored in a memory of the device itself. Such a memory may be susceptible to data losses, so that secure storage of the data cannot be guaranteed in the prior art.

According to the invention, the administration data which are generally available in analogue form, such as for example administration doses and administration time, are converted into digital administration data which can then be relayed by means of the wireless information transmitter means to an external display and/or storage medium for further processing. Display and/or storage media of this type may for example be personal computers or tablets or also smartphones, but naturally this list should not be seen as being definitive.

In this case, in a special embodiment of the invention, the power provided by the power generator unit can be used for storage of administration data on the information storage medium, whereas the power for transmitting the administration data to an external display and/or storage medium is provided by this external device.

According to a first advantageous embodiment of the invention, the wireless information transmitter means is designed as an RFID transponder or as a means for near-field transmission. Administration data can be transmitted wirelessly in a simple manner by means of such information transmitter means via radio signals, wherein a standardised radio protocol is provided by which the administration data or also additional information means can be transmitted at extremely low power with maximum security over distances up to 300 meters.

In this case, there are various possibilities for appropriate design of the power generator means. It is therefore conceivable to design the power generator means as an inductive element, a piezoelectric element, an electrostatic element, a flow element, a wireless receiver or the like. By means of such equipment, the necessary electrical power for operation of the device according to the invention can be generated or quickly provided respectively by the device itself. In this case, for example kinetic energy applied by the user can be converted by the power generator means, for example in the form of an electrostatic element, into electrical power. When a flow element is used, however, the flow of the pharmaceutical or of air inside the device according to the invention respectively or the reservoir or dispensing opening thereof respectively can be utilised in order to generate electrical power for operation of the device.

When an inductive element is used as a power generator means for converting mechanical energy into electrical power, it has proved as being advantageous to use a rotary generator or a linear generator or a microgenerator in which magnets and coils interact with one another inductively.

Furthermore, a capacitor can also be used as an electrostatic element for storage of the electrical power.

If the power generator means for converting mechanical energy into electrical power is designed as a piezoelectric element, it has proved advantageous that this element has at least one piezoelectric crystal.

If the power generator means is designed as a flow element for converting flow energy into electrical power, this element advantageously has a turbine or a vibration element.

Naturally it is also possible to design the power generator means as a wireless receiver for converting the energy of an electromagnetic field into electrical power.

According to a different concept of the invention, the information storage medium is designed as a counter by which triggering operations of the trigger means, or dosage units which have been administered by triggering of the trigger means, are added up or subtracted from a specific maximum value. As a result, it is possible in a simple manner to establish a total number of doses for the pharmaceutical located in the reservoir and to deduct the corresponding dosage units or triggering operations respectively therefrom or to add them correspondingly. As far as the total number of administered dosage units is close to the total amount of the pharmaceutical in the reservoir and thus the remaining doses located in the reservoir fall short of a threshold value, the device can inform the user of this automatically via the wireless information transmitter means. The user can then provide or obtain respectively a new reservoir in good time.

The device for administration of a pharmaceutical can be designed for example as a syringe means or also as an inhaler means.

Such inhaler means and syringe means are used regularly, if necessary a number of times daily, by many patients, in particular allergy sufferers and chronically sick people, so that the devices according to the invention may be very helpful to the user in the management of the pharmaceutical administration.

Therefore, in addition to the previously described device, a system consisting of a device of this type and an external display and/or storage medium is also protected, the external display and/or storage medium being designed for carrying out a documentation management and optionally having a microprocessor for this purpose. In this case, a corresponding software program or an application respectively by which the documentation management can be carried out can be installed on a personal computer or tablet or on a smartphone respectively which then functions as an external display and/or storage medium. For example, a program of this type or an application of this type respectively can also record the time, which may be particularly advantageous in particular for chronically sick patients. If a chronically sick patient measures corresponding body-related measured values and then self-administers a pharmaceutical with a device according to the invention, the device according to the invention then sends the data relating to this administered pharmaceutical to the software program or the application respectively which has already started. According to the invention, the time of administration of the pharmaceutical or the time of transmission of the measured value respectively is then documented by the software program or the application respectively. In this case, it is possible to dispense with a separate clock in the device according to the invention, so that the technical structure thereof is simplified.

Further objects, advantages, features and possible applications of the present invention are apparent from the following description of embodiments with reference to the drawings. In this case, all the features described and/or illustrated, considered alone or in any sensible combination, form the subject matter of the invention, also independently of their composition in the claims or their dependencies.

DETAILED DESCRIPTION

Figure 1:
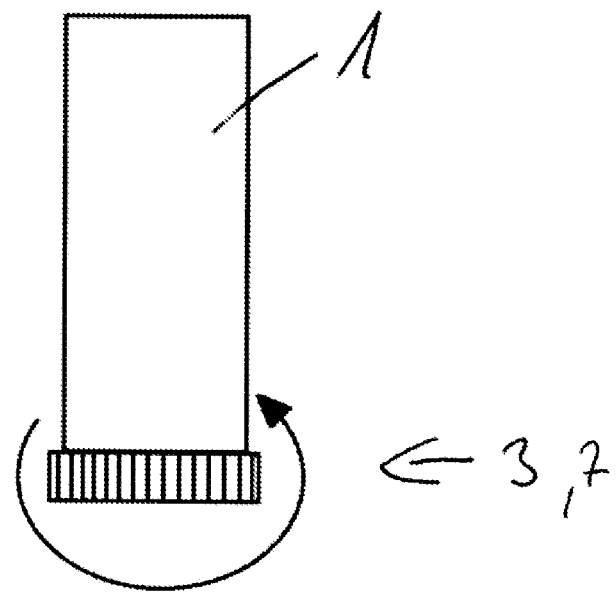
FIG. 1 shows a first embodiment of a device according to the invention.

A first embodiment of a device according to the invention for administration of a pharmaceutical is shown in FIG. 1. In the present case, this consists primarily of a reservoir 1 for storage of the pharmaceutical, the reservoir 1 having a dispensing opening (not shown here) at its upper end. In this respect, a trigger means 3 for triggering an administration of the pharmaceutical is provided at the lower end of the reservoir 1 in the drawing according to FIG. 1. As soon as this trigger means 3 is actuated by the user, the pharmaceutical is released through the dispensing opening (not shown here). Moreover, the power generator means 7 is disposed at the lower end of the reservoir 1 which in the present case is actuated by rotation of this lower end. When the power generator means of the device is rotated, an electrical current is induced by a coil (not shown here) and a magnet associated therewith, which current is sufficient for the supply of power to the device during administration both for converting analogue administration data into digital administration data and for transmitting these administration data to an external display and/or storage medium.

Figure 2:
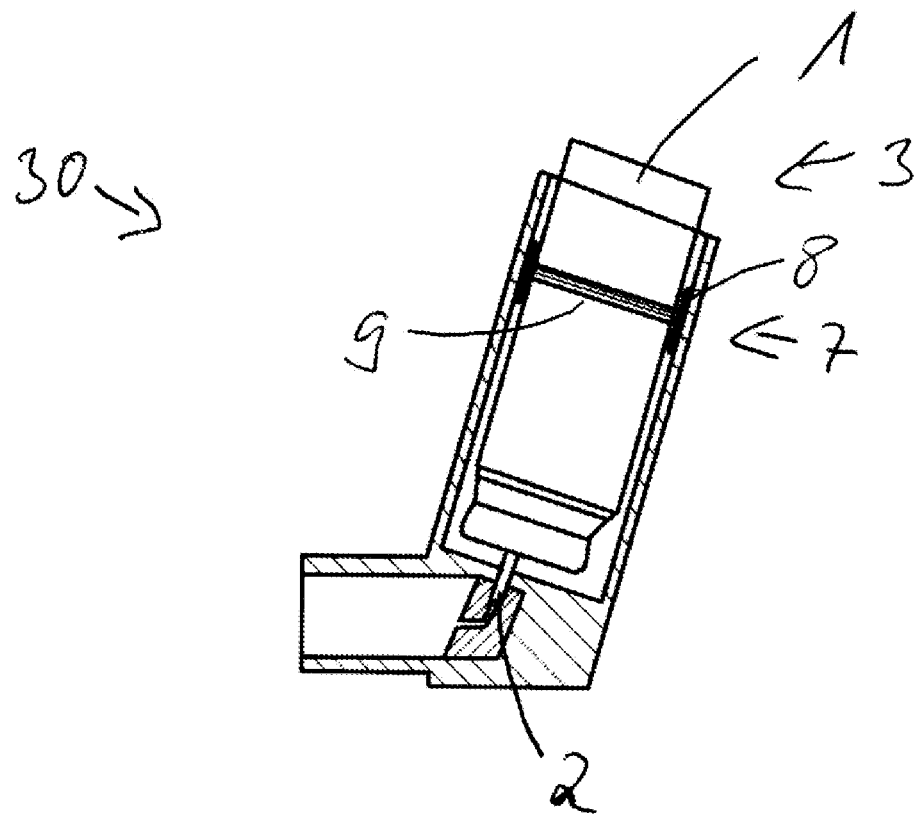
FIG. 2 shows a second embodiment of a device according to the invention.

In the embodiment shown in FIG. 2, an inhaler is shown as a device for administration of a pharmaceutical. A reservoir 1 having a pharmaceutical is accommodated in the main body of the inhaler, at the lower end of which there is a dispensing opening 2 for the pharmaceutical. The upper end of the reservoir 1 serves at the same time as a trigger means 3 for triggering an administration of a pharmaceutical. Two magnets 8 which co-operate with a coil 9 disposed on the reservoir 1 are disposed on the main body of the inhaler. As soon as the inhaler is to carry out an administration, the trigger means 3 of the reservoir 1 is actuated by the user. To this end, the reservoir is moved in the downwards direction within the main body of the inhaler. In this case, not only is the passage for the pharmaceutical through the dispensing opening opened, but also the movement of the coil 9 associated with the reservoir 1 relative to the magnet 8 associated with the main body of the inhaler induces an electrical current which is sufficient for supplying electrical power both to a converter means (not shown here) for converting analogue administration data into digital administration data and an information transmitter means (likewise not shown here) for wireless transmission of the administration data to an external memory and/or display medium.

Figure 3:
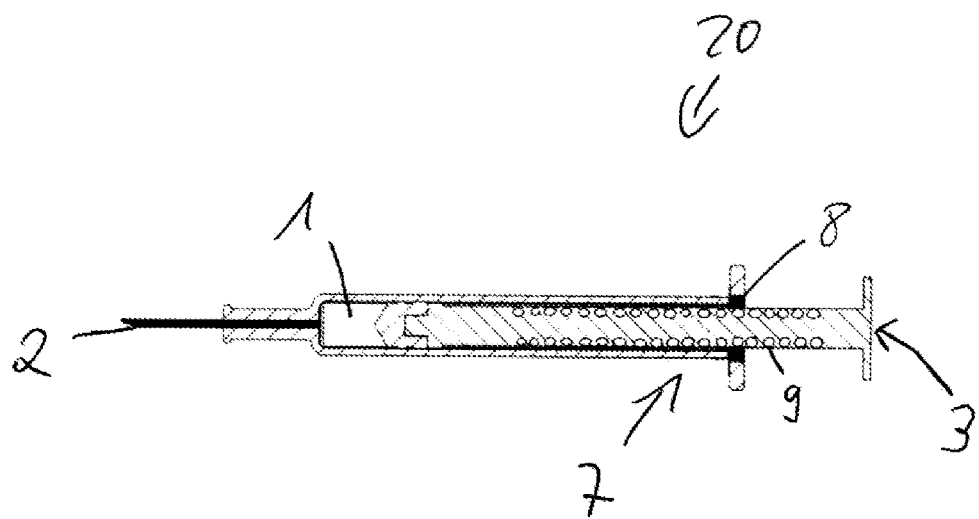
FIG. 3 shows a third embodiment of a device according to the invention.

In the embodiment according to FIG. 3, the mode of operation corresponds to that of FIG. 2. However, it does not relate to an inhaler but to a syringe. On the body of the syringe are disposed magnets 8 which interact inductively with a coil 9 which is associated with the piston of the syringe and one end of which also serves as a trigger means. The tip of the syringe serves as the dispensing opening of this device for administration of a pharmaceutical.

Figure 4:
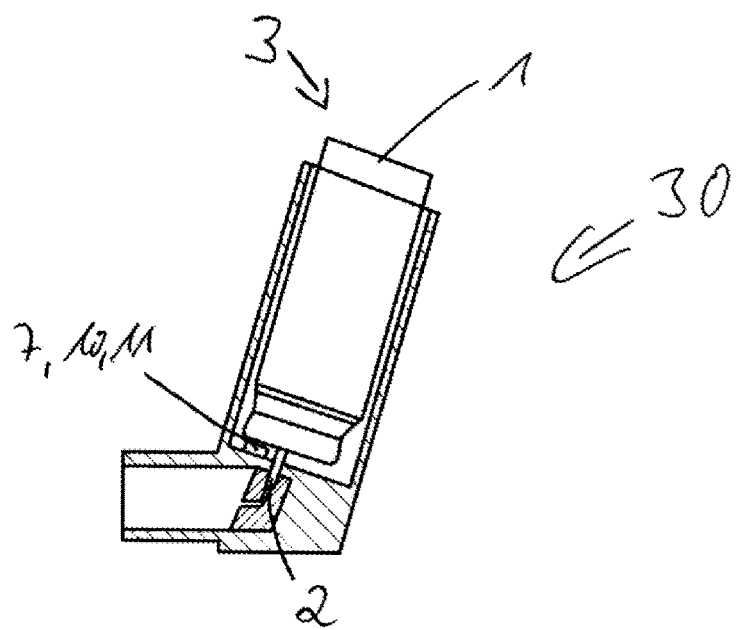
FIG. 4 shows a fourth embodiment of a device according to the invention.

The embodiment of FIG. 4 again relates to an inhaler for dispensing a pharmaceutical, substantially corresponding to that of FIG. 2. However, in this case the electrical power necessary for operation of the converter means 5 and the information transmitter means 6 is not generated inductively via a magnet/coil combination. Instead, in this case a piezoelectric element 10 with a piezoelectric crystal 11 is used, which when the trigger means 3 is actuated at the upper end of the reservoir 1 comes into contact with the lower end of the reservoir 1 and in this respect generates the electrical power for operating the device according to the invention. In this case, the drug or pharmaceutical is dispensed again via the dispensing opening 2 at the lower end of the reservoir 1 which is retained in the main body of the inhaler.

Figure 5:
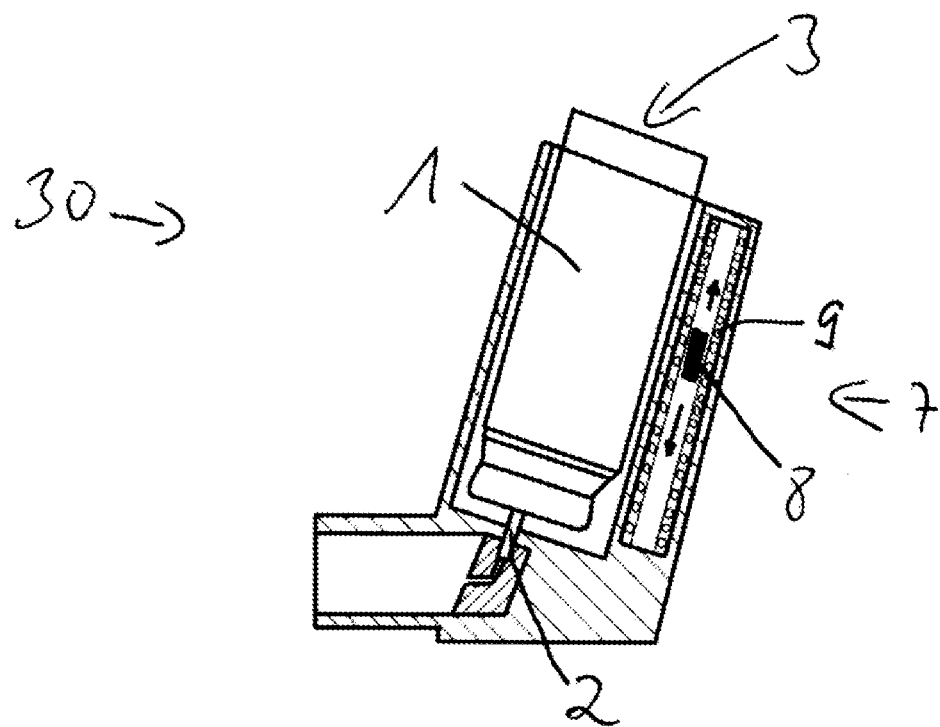
FIG. 5 shows a fifth embodiment of a device according to the invention.

The embodiment according to FIG. 5 for energy generation again employs the law of induction. In this connection, however, a coil 9 is not moved relative to a magnet 8. On the contrary, the magnet 8 there is moved relative to the coil 9 integrated in the main body of the inhaler, for example by shaking of the inhaler, so that the necessary electrical power is generated within the coil 9 for operation of the device, in particular of the converter means and information transmitter means. In this case, the coil 9 and the magnet 8 form the power generator means 7. This is therefore advantageous in particular since specific inhalers usually have to be shaken before use.

Figure 6:
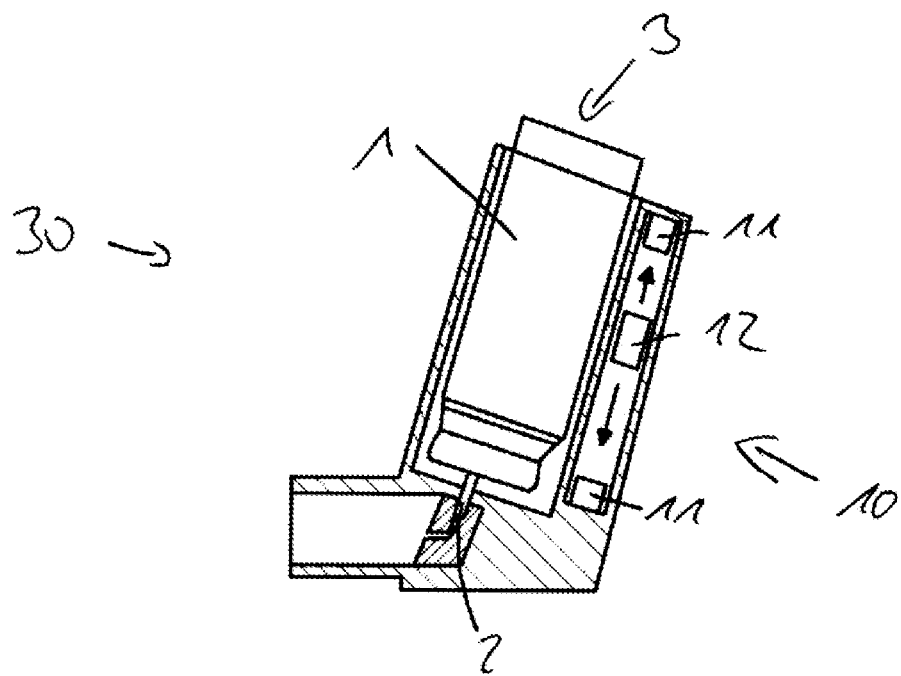
FIG. 6 shows a sixth embodiment of a device according to the invention.

In the embodiment according to FIG. 6, the electrical power is obtained in a similar manner to that of the embodiment according to FIG. 5. However, in this case no coil/magnet combination is used for electrical power generation. Instead, a piezoelectric element 10 is used which in this case is formed with two piezoelectric crystals 11 and a bolt 12 which oscillates between them. As soon as the bolt 12 strikes one of the piezoelectric crystals, for example when the inhaler is shaken, an electrical current is generated therein or thereby respectively which is sufficient for operation of the device for dispensing a pharmaceutical, in particular the converter means thereof and the information transmitter means thereof.

Figure 7:
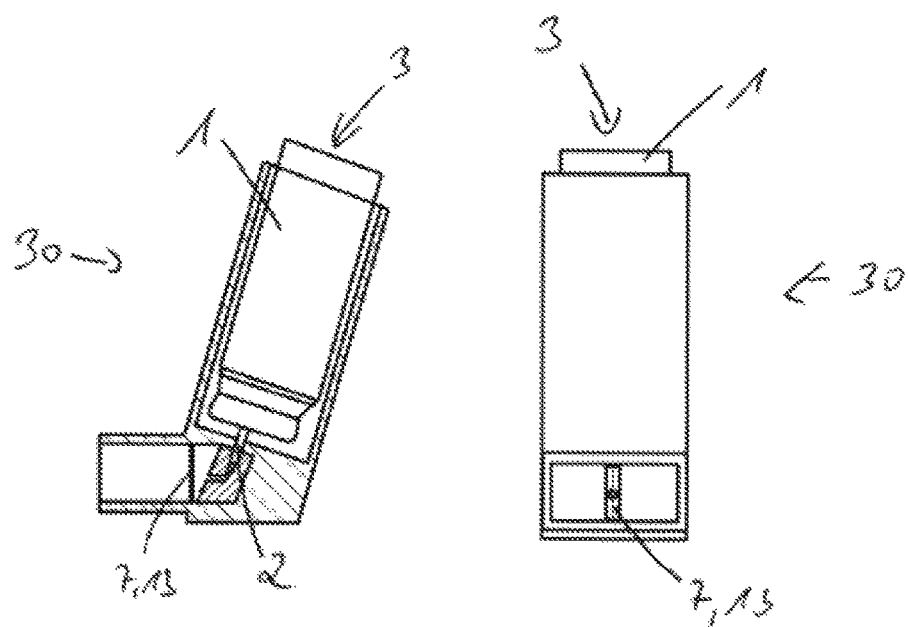
FIG. 7 provides different views of a seventh embodiment of a device according to the invention.

In the embodiment according to FIG. 7, the electrical power is generated by an element 13 excited to vibration which is disposed in an outlet opening of the inhaler 30 there and is excited to vibration by the pharmaceutical flowing out. In this respect, the trigger mechanism corresponds to the devices designed as an inhaler 30 for dispensing a pharmaceutical according to FIGS. 1, 2, and 4 to 6.

If the flow generated by the expulsion of the drug or pharmaceutical respectively is not sufficient for setting the rotor 13 in operation, this can also take place by the user drawing air out of the inhaler. Furthermore, it may also be possible to use instead of the rotor 13 a flexible vibration element which is excited to vibration by the previously described air flow. Although such vibration elements are already known from the prior art, they can also be used in the device according to the invention in a simple manner in order to obtain electrical power for operation of this device.

Figure 8:
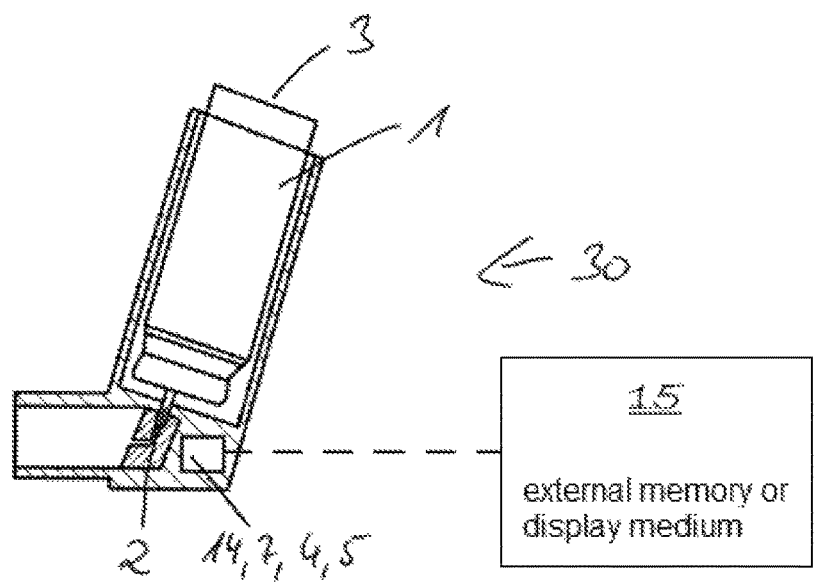
FIG. 8 shows an eighth embodiment.

In FIG. 8 an inhaler 30 is again shown schematically, a reservoir 1 for a pharmaceutical being disposed in the main body. By actuation of the end of the reservoir 1 which is designed as a trigger means 3 and projects out of the main body the pharmaceutical administration is started, the pharmaceutical being able to escape out of the inhaler through a dispensing opening 2 at the other end of the reservoir 1. An information transmitter means 6 designed as a wireless receiver 14 is indicated schematically on the inhaler and serves to transmit administration data wirelessly to an external memory and/or display medium 15.

Naturally, for interim storage an inhaler of this type—also one of the inhalers previously described in the embodiments—can be equipped with an information storage medium 4.

This drawing likewise only indicates the converter means 5 for conversion of analogue administration data into digital administration data and the power generator means 7 which as described above may be configured in various ways.

Figure 9:
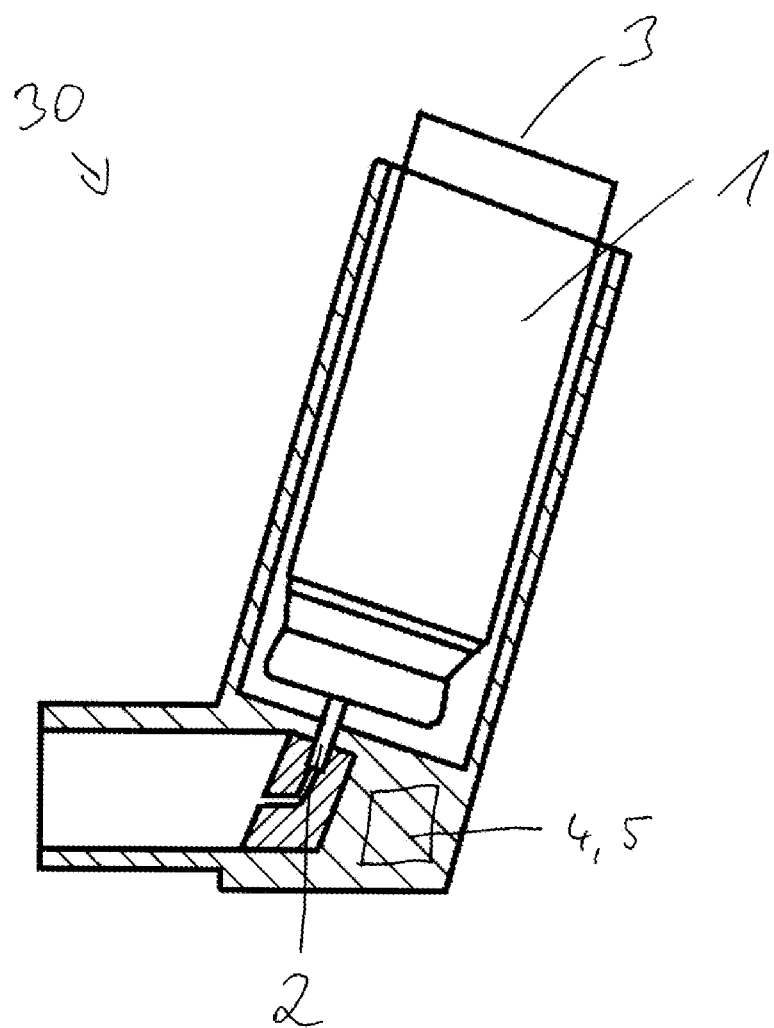
FIG. 9 shows a ninth embodiment of a device according to the invention.

A similar embodiment is shown in FIG. 9, in which the information storage medium 4 and the converter means 5 are configured separately from the power generator means 7 and the information transmitter means 6 designed as a wireless receiver 14.

LIST OF REFERENCE NUMERALS 1 reservoir
2. dispensing opening
3 trigger means
4 information storage medium
5 converter means
6 information transmitter means
7 power generator means
8 magnet
9 coil
10 piezoelectric element
11 piezoelectric crystal
12 bolt
13 element 14 wireless receiver
20 syringe means
30 inhaler means

The invention claimed is:

1. A device for administration of a pharmaceutical comprising
   a) a reservoir for storage of the pharmaceutical, wherein the reservoir has a dispensing opening;
   b) a trigger for triggering an administration of a pharmaceutical, in which the pharmaceutical is dispensed through the dispensing opening;
   c) an information storage medium for storage of administration data;
   d) a converter for converting analogue administration data into digital administration data,
   e) a wireless information transmitter for transmitting the administration data to an external display and/or storage medium; and
   f) a power generator for providing electrical power for the converter, information storage medium and/or the information transmitter,
   wherein required power is obtained by the power generator during administration of the pharmaceutical instead of obtaining the power from a long-term power storage unit, and wherein the required power is provided to the converter, information storage medium and/or the information transmitter only during the administration of the pharmaceutical.

2. The device according to claim 1, wherein the wireless information transmitter comprises an RFID transponder, or a near-field transmitter.

3. The device according to claim 1, wherein the power generator comprises an inductive element for converting mechanical energy into electrical power, wherein the converting is performed by use of a rotary generator, wherein by rotating the power generator, an electrical current is induced by a coil and a magnet associated therewith by rotating the coil and the magnet against each other.

4. The device according to claim 1, wherein the power generator comprises a piezoelectric element for converting mechanical energy into electrical power, wherein the piezoelectric element comprises at least one piezoelectric crystal, which when the trigger is actuated at an upper end of the reservoir, the at least one piezoelectric crystal comes into contact with a lower end of the reservoir and thereby generates electrical power.

5. The device according to claim 1, wherein the power generator comprises a flow element for converting flow energy into electrical power, wherein the flow element comprises a turbine or a vibration element.

6. The device according to claim 1, wherein the power generator further comprises a wireless receiver for converting energy of an electromagnetic field into electrical power.

7. The device according to claim 1, wherein the information storage medium is designed as a counter by which triggering operations of the trigger, or dosage units which have been administered by triggering of the trigger, are added up or subtracted from a predetermined maximum value.

8. The device according to claim 1, wherein the device is a syringe, or an inhaler.

9. A system comprising:
   the device of claim 1; and
   at least one of an external display and a storage medium; wherein the at least one of the external display and the storage medium is designed for carrying out a documentation management.

10. The system according to claim 9, wherein the at least one of the external display and the storage medium comprises a personal computer, or a tablet, or a smartphone, and wherein the documentation management comprises a software program, or an application, wherein the software program is stored on the personal computer, or the tablet, or the smartphone.

11. The device according to claim 1, wherein the device does not contain a battery and/or does not contain an accumulator.

12. The device according to claim 1, wherein at least one magnet is disposed on a main body of the device and a coil is disposed on the reservoir, the reservoir being accommodated in the main body, wherein during administration the reservoir is moved relative to the main body and the coil is moved relative to the magnet, thereby inducing an electrical current.

* * * * *